(12) United States Patent
Florkiewicz

(10) Patent No.: US 6,281,197 B1
(45) Date of Patent: Aug. 28, 2001

(54) CARDIAC GLYCOSIDES AND THEIR AGLYCONE DERIVATIVES TREAT COMPLICATIONS OF DIABETES

(75) Inventor: Robert Z. Florkiewicz, Ramona, CA (US)

(73) Assignee: Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/466,036

(22) Filed: Dec. 17, 1999

Related U.S. Application Data

(60) Continuation of application No. 09/322,676, filed on May 28, 1999, now Pat. No. 6,107,283, which is a division of application No. 09/211,290, filed on Dec. 14, 1998, now Pat. No. 6,071,885, which is a division of application No. 08/599,895, filed on Feb. 12, 1996, now Pat. No. 5,891,855.

(51) Int. Cl.[7] ........................ A61K 31/705; A01N 45/00; C07K 1/00

(52) U.S. Cl. ............................... 514/26; 514/25; 514/27; 514/28; 514/29; 514/30; 514/31; 435/184; 530/351; 530/396; 530/399

(58) Field of Search .................................. 514/26, 25, 27, 514/28, 29, 30, 31; 435/184; 530/351, 396, 399

(56) References Cited

U.S. PATENT DOCUMENTS

| | | | |
|---|---|---|---|
| 5,545,623 | * | 8/1996 | Matsumori ............................. 514/26 |
| 5,627,195 | * | 5/1997 | Hu ....................................... 514/321 |
| 5,872,103 | * | 2/1999 | Belletti .................................. 514/26 |

FOREIGN PATENT DOCUMENTS

WO 96/04291  2/1996  (WO) .

OTHER PUBLICATIONS

Katahira et al. *Chemotherapy* Jul. 1991, 39(7), 678–686.*
Callard et al. "The Cytokine FactsBook" Academic Press Limited, London, 1994, pp. 31–38.*
Brooks, D., "Protein Secretion by the Rat Epididymis Can Be Selectively Modified in Vitro by Local Anesthetics, Glucose Deprivation, Dinitrophenol, Ouabain and Ionophores," *J. Androl.* 5: 351–360, 1984.
Cooper and Barondes, "Evidence for Export of a Muscle Lectin from Cytosol to Extracellular Matrix and for a Novel Secretory Mechanism," *Journal of Cell Biology* 110:1681–1691, 1990.

Crutchely and Smariga, "Monovalent Cation Dependence of Tissue Plasminogen Activator Synthesis by HeLa Cells," *Journal of Biological Chemistry* 262(7): 3017–3021, 1987.
Florkiewicz et al., "Multiple Forms of bFGF: Differential Nuclear and Cell Surface Localizaton," *Growth Factors* 4:265–275, 1991.
Florkiewicz et al., "Quantitative Export of FGF–2 Occurs Through an Alternative, Energy–Dependent, Non–ER/Golgi Pathway," *Journal of Cellular Physiology* 162: 388–399, 1995.
Jackson et al., "Heath shock induces the release of fibroblast growth factor 1 from NIH 3T3 cells, " *Proc. Natl. Acad. Sci. USA* 89: 10691–10695, 1992.
Jackson et al., "The Release of Fibroblast Growth Factor–1 from NIH 3T3 Cells In Response to Temperature Involves the Function of Cysteine Residues," *Journal of Biological Chemisty* 270(1): 33–36, 1995.
Mignatti et al., "Basic Fibroblast Growth Factor, a Protein Devoid of Secretory Signal Sequence, Is Released by Cells via a Pathway Independent of the Endoplasmic Reticulum–Golgi Complex,"*Journal of Cellular Physiology 151*: 81–93, 1992.
Repke et al., "Potential suitablility of NA(^+) /K(^+) –transporting ATPase in pre–screens for anti–cancer agents," *Anti–Cancer Drug Design 10*: 177–187, 1995.
Rubartelli et al., "A novel secretory pathway for interleukin–1.beta., a protein lackin a signal sequence," *EMBO Journal* 9(5): 1503–1510, 1990.
Rubartelli et al., "Post–Translational Regulation of Interleukin 1.beta. Secretion,"*Cytokine* 5(2): 117–134, 1993.
Rubartelli et al., "Secretion of Thioredoxin by Normal and Neoplastic Cells through a Leaderless Secretory Pathway," *Journal of Biological Chemistry* 267(34): 24161–14164, 1992.
Siders and Mizel, "Interleukin–1.beta. Secretion. A Possilbe Multistep Process that is Regulated in a Cell Type–Specific Manner," *Journal of Biological Chemistry* 270(27):16258–16264, 1995.

* cited by examiner

Primary Examiner—Kathleen K. Fonda
(74) *Attorney, Agent, or Firm*—Seed Intellectual Property Law Group PLLC

(57) ABSTRACT

This invention provides methods of inhibiting the export of a leaderless protein from a cell by contacting the cell with a cardiac glycoside or aglycone derivative. Leaderless proteins include FGF-1, FGF-2, IL-1α, IL-1β and factor XIIIa. These methods are useful in treatment of conditions, including tumors and diabetes.

7 Claims, 6 Drawing Sheets

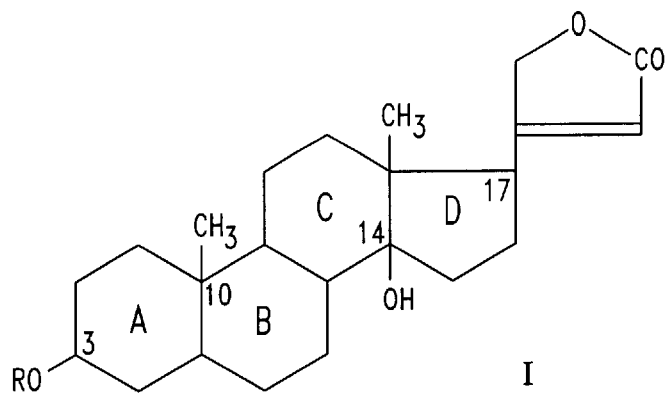

*Lanatoside A* (Digilanide A): R = (digitoxose)$_3$-D- glucose + acetyl.
 (Naturally occurring in *Digitalis lanata, Digitalis ferruginea*.)
*Desacetyllanatoside A* (Purpuren Glycoside A): R = (digitoxose)$_3$-D-glucose.
 (Naturally occurring in *Digitalis purpurea* or from Lanatoside A by hydrolysis with mild alkali.)
*Acetyl Digitoxin*: R = (digitoxose)$_3$+acetyl. (Derived from Lanatoside A by enzymatic action.)
*Digitoxin*: R = (digitoxose)$_3$. (In *Digitalis purpurea* and *Digitalis lanata* by enzymatic breakdoown of Purpuren Glycoside A or Lanatoside A.)

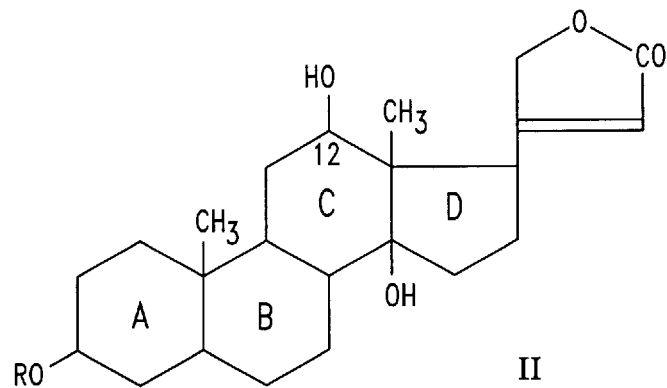

*Lanatoside C*: R = (digitoxose)$_3$-D- glucose + acetyl.
 (Naturally occurring in *Digitalis lanata*.)
*Desacetyllanatoside C*: R = (digitoxose)$_3$-D- glucose.
 (Derived from Lanatoside C by hydrolysis with mild alkali.)
*Digoxin* R = (digitoxose)$_3$. (In *Digitalis lanata* by enzymatic breakdoown of Lanatoside C.)

*Fig. 1A*

*Strophanthoside*: R = cymarose-b -D glucose-a -D glucose (In *Strophanthus Kombe.*)
K-*Strophanthin*: R = cymarose-b -D-glucose (In *Strophanthus Kombe.*)

*Ouabain* (g-strophanthin) R = L-rhamnose (In *Strophanthus gratus.*)

*Scillaren A*: R = L-rhamnose-D-glucose (In *Scilla maritima.*)
*Proscillaridin A*: R = L-rhamnose (*Scilla maritima.*)

CARDIAC GLYCOSIDES AND THEIR AGLYCONE DERIVATIVES TREAT COMPLICATIONS OF DIABETES

CROSS-REFERENCE TO RELATED APPLICATIONS

This application is a continuation of U.S. patent application Ser. No. 09/322,676, filed May 28, 1999, and issued as U.S. Pat. No. 6,107,283 on Aug. 22, 2000; which is a divisional of U.S. patent application Ser. No. 09/211,290, filed Dec. 14 1998, and issued as U.S. Pat. No. 6,071,885 on Jun. 6, 2000; which is a divisional of U.S. patent application Ser. No. 08/599,895, filed Feb. 12, 1996, and issued as U.S. Pat. No. 5,891,855 on Apr. 6, 1999.

TECHNICAL FIELD

The present invention relates generally to inhibitors of leaderless protein export, and more specifically, to the use of cardiac glycosides and aglycone derivatives to inhibit export of leaderless proteins into extracellular spaces.

BACKGROUND OF THE INVENTION

Many proteins exert an effect on cell growth, differentiation, and inflammation through signal transduction, mediated by binding to a cell surface receptor. Yet other proteins such as factors that initiate or are necessary the blood clot formation act enzymatically in blood. While these actions are generally part of normal processes, under certain circumstances, it may be desirable to limit or inhibit the action of certain proteins and the effects of subsequent signaling. For example, tumor growth promoted by a growth factor, such as bFGF acting on melanoma cells, is deleterious and often leads to fatalities.

Approaches to inhibit specific proteins have concentrated primarily on interfering with protein-substrate or protein-receptor interactions. Typically, this involves using an antibody or other molecule that competitively binds the protein, by administration of competitors for receptor binding, or by protease digestion of the protein. An alternative approach, not generally pursued, is to reduce the level of the protein by inhibiting its expression at a transcriptional or translational level. Methods of reducing protein levels by inhibiting the trascription or translation of the protein have been difficult to achieve because of inherent problems of inhibiting the specific expression of one or a few proteins.

The discovery that certain proteins, such as growth factors, mediators of inflammation, and mediators of blood clotting, are exported through a nonclassical secretory pathway allows the development of specific inhibitors for these proteins. These proteins are identified by their lack of a hydrophobic leader sequence that mediates secretion by the classical Golgi/ER pathway. These proteins are believed to be exported from a cell by exocytosis.

This invention provides inhibitors of the export of these leaderless proteins, allowing control of undesired proliferation and inflammation, as well as other related advantages.

SUMMARY OF THE INVENTION

The present invention generally provides methods of inhibiting the export of a leaderless protein from a cell expressing the protein. In one aspect of the invention, export is inhibited by contacting a cell expressing the protein with a cardiac glycoside. In certain embodiments, the cardiac glycoside is selected from the group consisting of digoxin, strophantin K, digitoxin, lanatoside A and ouabain. Preferably the cardiac glycoside is ouabain or digoxin.

In another aspect of the invention, methods of inhibiting the export of a leaderless protein from a cell expressing the protein by contacting the cell with an aglycone derivative of a cardiac glycoside are provided. In certain embodiments, the aglycone derivative is selected from the group consisting of digoxigenin, digitoxigenin and uzarigenin. Preferably the aglycone derivative is digoxigenin.

In other aspects, methods are provided for inhibiting the export of FGF-2 from a cell expressing FGF-2, comprising contacting the cell with a cardiac glycoside or aglycone derivative of a cardiac glycoside. In yet other aspects, methods of treating an FGF-mediated pathophysiological condition in a patient are provided, comprising administering a therapeutically effective dosage of a cardiac glycoside or aglycone derivative of a cardiac glycoside, thereby reducing the amount of FGF-2 that is exported. In certain embodiments, the pathophysiological condition is melanoma, ovarian carcinoma, tetracarcinoma and neuroblastoma.

In yet other aspects, methods are provided for inhibiting proliferation of a cell bearing an FGF receptor, comprising contacting the cell with a cardiac glycoside or an aglycone derivative of a cardiac glucoside. In still other aspects, methods are provided for treating complications of diabetes, comprising contacting a cell with an inhibiting amount of a cardiac glycoside or aglycone derivative.

Methods are also provided for inhibiting export of leaderless proteins, comprising treating cells with a compound selected from the group consisting of formula 1, formula 2, formula 3, formula 4, or formula 5.

These and other aspects of the present invention will become evident upon reference to the following detailed description and attached drawings. Various references are set forth below which described in more detail certain procedures or compositions (e.g., plasmids, etc.). All of these references are incorporated by reference in their entirety.

DETAILED DESCRIPTION OF THE INVENTION

As an aid to understanding the invention, certain definitions are provided herein.

Figure 1B:
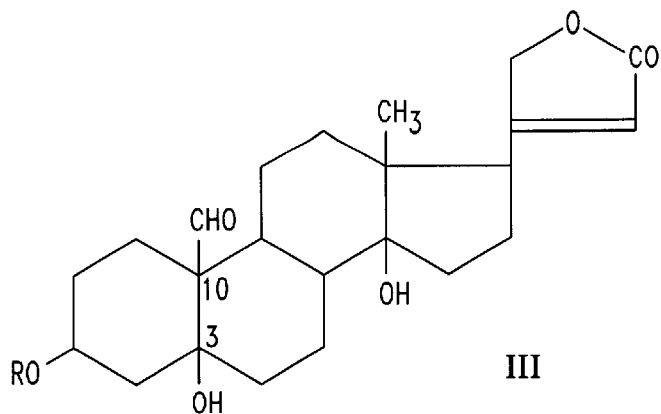
FIG. 1 is a drawing of the general structure of the aglycone nucleus of various cardiac glycosides.
Figure 1B:
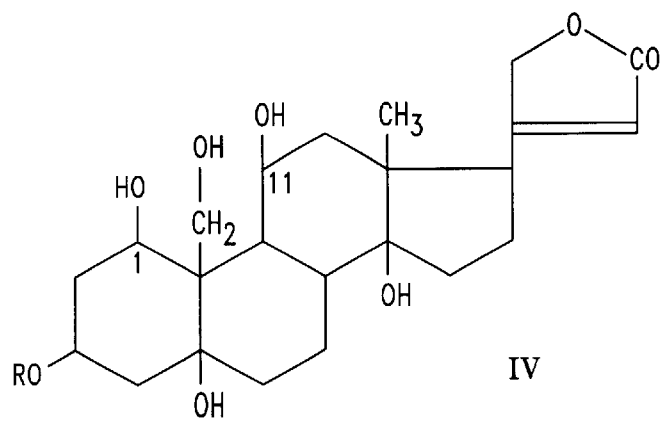
Figure 1B:
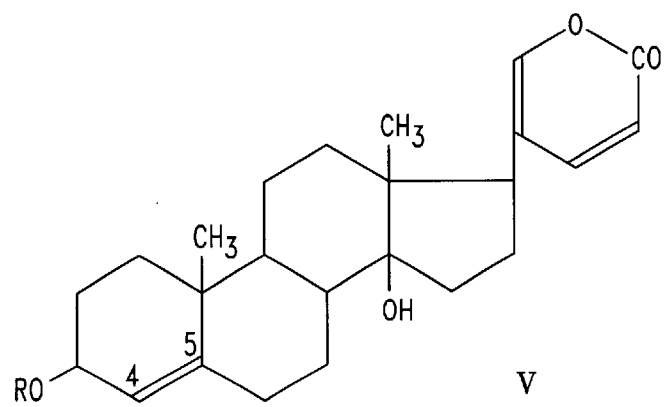

"Cardiac glycoside" refers to a group of compounds which are structurally related. Structurally, these compounds are derived from the cyclopentanoperhydro-phenanthrene nucleus characteristic of steroid compounds, have a five-membered unsaturated lactone ring of a six-membered doubly unsaturated lactone ring at C17 of ring D, a hydroxyl group at C3 in ring A for joining by an ether linkage to one or more sugar residues, and a hydroxy group at C14 (FIG. 1). The aglycone derivatives of cardiac glycosides have a similar structure, but lack the carbohydrates characterstic of the cardiac glycosides. These aglycone derivatives are also useful in the present invention. Representatives of this group are found in a number of botanical sources, as well as in mammals. (See, *A survey of Cardiac Glycosides and Genins*, University of South Carolina Press, 1961.) The cardiac glycosides include ouabain-like/digoxin-like compounds that have been isolated from mammals (see, U.S. Pat. No. 4,780,314).

"Leaderless protein" refers to a protein or polypeptide that arrives in an extracellular environment but lacks a canonical leader sequence. A leader sequence mediates translocation into the ER and is recognized by signal recognition proteins (SRP). Proteins in the extracellular environment include secreted proteins found in extracellular spaces, as well as proteins that are membrane bound, but not an integral membrane protein. The prototypic leader sequence has an amino-terminal positively charged region, a central hydrophobix region, and a more polar carboxy-terminal region (see, Von Heijne, *J. Membrane Biol.* 115:195–201, 1990). Leaderless proteins include FGF-1, FGF-2, interleukin 1α, interleukin 1β, vas deferens protein, platelet-derived endothelial cell growth factor, ciliary neurotrophic factor, thymosin, parathymosin, 14.5 kDa lectin (L14), transglutaminase, thioredoxin-like protein, sciatic nerve growth-promoting activity, factor XIIIa, and int-2. Within the context of their invention, leaderless proteins include naturally occurring proteins as well as proteins that are engineered to lack a leader sequence, but are exported. The terms "signal sequence," "leader peptide," and "leader sequence" are used interchangeably herein.

"Export" of a potein refers to a metabolically active process of transporting a translated cellular product to the extracellular spaces or at the cell membrane by a mechanism other than by a leader sequence.

Leaderless Proteins

As noted above, leaderless proteins are proteins that arrive in the extracellular environment but lack a signal sequence which functions to mediate translation of a protein into the ER b SRP recognition. Typically, these proteins are initially identified because their primary translation product lacks a canonical hydrophobic leader or signal sequence, which is usually located at the N-terminus of the primary translation product and is used in the transport process through the Golgi/ER. A leader sequence has three distinct domains: an amino-terminal positively charged region approximately 1–5 residues long; a central, hydrophobic region approximately 7–15 residues long; and a more polar carboxy-terminal domain approximately 3–7 residues long (von Heijne, supra). The hydrophobic central region is critical.

Several leaderless proteins have been identified by virtue of their location in the extracellular environment, transport by a mechanism other than through the Golgi/ER, and lack of a leader sequence. Such proteins include IL-1α (SEQ ID NOS: 4,5; precursor, mature forms), IL-1β (SEQ ID NOS: 6, 7; precursor; mature forms), FGF-1, FGF-2 (SEQ ID NO: 1,2; cDNA, 18 kD form), PD-ECGF (platelet-derived endothelial cell growth factor), CNTF (ciliary nutrotrophic factor), sciatic nerve growth-promoting activity, vas deferens protein, transglutaminiase, L-14 lectin, factor XIIIa, thioredoxin-like protein (ADF), thymosin, parathymosin, and int-2.

Other leaderless proteins that are exported may be identified by a two-part assay: (1) identification of the protein in extracellular spaces, including at the membrane, and (2)brefeldin-resistant export. A preliminary assessment to identify candidate leaderless proteins may be made by inspection of the amino acid sequence of the primary translation product. Comparison of the amino-terminal sequence with other known leader sequences or identification of the prototypic pattern sequence, as described herein (von Heijne, supra), provides a means to classify potential leaderless proteins. As discussed above, leader sequences are approximately 15–25 amino acids long and contain at minimum a central region of 7–15 hydrophobic residues, such as leucine, isoleucine, valine, glycine, phenylalanine, methionine, threonine, serine, proline, cysteine, alanine, tyrosine, and tryptophan. Any primary translation sequence of a protein that lacks such a sequence is a candidate for an exported leaderless protein.

As noted above, identification of a protein as a leaderless protein rests in the two-part assay, discovery of the protein in the extracellular environment and brefeldin-resistance.

The first assay is performed to detect the protein extracellularly. For this assay, test cells expressing a leaderless protein are necessary. Either the test cells may naturally produce the protein or preferably produce it from a transfected expression vector. For FGF-2 expression, CO5 cells are preferred for transfection. For expression of IL-1, p388D1 cells are preferred. Following expression, the protein is detected by any one of a variety of well known methods and procedures. Such methods include straining with antibodies in conjunction with flow cytometry, confocal microscopy, image analysis, immunoprecipitation of cell medium, Western blot of cell medium, ELISA, or bioassay. A preferred assay during initial screening is ELISA. Any candidate is confirmed by one of the other assays, preferably by immunoprecipitation of cell medium following metabolic labeling. Briefly, cells expressing the candidate leaderless protein are pulse labeled for 15 min with $^{35}$S-methionine and/or $^{35}$S-cysteine in methionine and/or cystein free medium and chased in medium supplemented with excess methionine and/or cysteine. Medium fractions are collected and clarified by centrifugtion in a microfuge. Lysis buffer containing 1% NP-40, 0.5% deoxycholate (DOC), 20 mM Tris, pH 7.5 5 mM EDTA, 2 mM EDGTA, 10 nM PMSF, 10 ng/ml aprotinin, 10 ng/ml leupeptin, and 10 ng/ml pepstatin is added to the clarified medium to inhibit proteases. Antibody to the candidate leaderless protein is added and following incubation in the cold, a precipitating second antibody or immunoglobulin binding protein, such as protein A-Sepharose® or GammaBind™-Sepharose® is added for further incubation. In parallel, as a control, a vector encoding a cytosolic protein is co-transfected and an antibody to a known cytosolic protein is used in immunoprecipitations. Immune complexes are pelleted and washed with ice-cold lysis buffer. Complexes are further washed with ice-cold IP buffer (0.15 M NaCl, 10 mM Na-phosphate, pH 7.2, 1% DOC, 1% NP-40, 0.1% SDS). Immune complexes are eluted directly into SDS-gel sample buffer and electrophoresed in SDS-PAGE. The percentage of acrylamide will depend upon the molecular weight of the leaderless protein. The gel is processed for fluorography, dried and exposed to X-ray film. Proteins that are expressed at higher levels in medium as compared to the cytosolic protein control are tested for brefeldin resistant export.

Brefeldin-resistant is measured in cells expressing a leaderless protein as described above. Briefly, cells, such as COS-1 cells are transfected with an expression vector directing expression of the leaderless protein, such as FGF-2. Approximately 2 days later, the transfected cells are metabolically pulse-labeled for 15 min with $^{35}$S-methionine and $^{35}$S-cysteine in met and cys free media. Label is removed, and the cells are further incubated in medium containing 15 $\mu$g/ml brefeldin A. For quantitation of FGF-2 export, 25 $\mu$g/ml heparin is added to the chase medium. Lack of statistically significant reduction in FGF-2 export indicates that protein export is brefeldin A resistant.

Inhibitors

As described above, cardiac glycosides and aglycones are inhibitors of the export of leaderless proteins. Cardiac glycosides and their aglycone derivatives are derived from the cyclopentanoperhydro-phenanthrene nucleus characteristic of steroid compounds (FIG. 1). At C17 of ring D, there is a five-membered unsaturated lactone ring or a six-membered doubly unsaturated lactone ring. At C3 on Ring A, there is a hydroxyl-group for joining to one or more sugar residues by an ether linkage, and at C14 there is a hydroxy group. In addition, other C atoms, such as C16, may have side groups. The sugar groups at C3 include monosaccharides, including glucose, rhamnose, cymarose, di-, tri, and polysaccharides, including cymarose-$\beta$-D-glucose, L-rhamnose-D-glucose, tridigitoxose, digitoxose$_3$-D-glucose, and the like, as well as sacchride derivatives. Aglycone derivatives have a similar structure to the cardiac glycosides, but lack the carbohydrate residue(s). However, other side groups may be substituted at the C3 position in aglycone derivatives. Together, cardiac glycosides and aglycone derivatives are classified as cardenolides.

Cardiac glycosides useful in the present invention include, but are not limited to, lanatoside A, desacretyllanatoside A, actyl digitoxin, digitoxin, lanatoside C, desacetyl-lanatoside C, digoxin, strophanthoside K-strophanthin, ouabain, scillaren A, proscillaridin A, uzarin, digitoxose, gitoxin, strophanthidine-3$\beta$-digitoxoside, strophanthidin $\alpha$-L-rhamnopyranoside, strophanthidol, oleandrin, acovenoside A, strophanthidine digilanobioside, strophanthidin-D-cymaroside, digitoxigenin-L-rhamnoside digitoxigenin theretoside, and the like. Aglycones include, but are not limited to, strophanthidin, digitoxigenin, uzarigenin, digoxigenin, digoxigenin 3,12-diacetate, gitoxigenin, gitoxigenin 3-acetate, gitoxigenin 3,16-diacetate, 16-acetyl gitoxigenin, acetyl strophanthidin, ouabagenin. 3-epidigoxigenin, and the like. Preferably the cardiac glycoside is ouabain, digoxin, or digitoxin. Most preferably, the cardiac glycoside is ouabain, and the aglycone derivative is strophanthidin.

Cardiac glycosides and aglycones may be purified from organisms, such as plants, or from human serum or urine. (see, for example, references in Merck Index, Tenth Edition; PCT application WO91/17176; U.S. Pat. No. 4,780,314; Kelly et al., *Kidney Int'l* 30:723–729, 1986). The compounds may also be purchased commercially (e.g., Sigma Chemical Co., St. Louis, Mo.; Calbiochem. San Diego, Calif.).

Assays for Detecting Inhibition of Export of Leaderless Proteins

Cardiac glycoside of aglycone derivative inhibitors of export of leaderless proteins are identified by one of the assays described herein. Briefly, a cell expressing a leaderless protein is treated with the cardiac glycoside or aglycone derivative and the amount of leaderless protein detected as an extracellular protein is compared to the amount detected without treatment.

Within the context of the present invention, an inhibitor must meet three criteria: (1) it blocks export of a leaderless protein, (2) it does not block export of a secreted protein with a leader sequence, and (3) it does not promote expression of a cytosolic protein in the extracellular environment.

In any of the assays described herein, the test cell may express the leaderless protein either naturally or following introduction of a recombinant DNA molecule encoding the protein. Similarly, the expression of the secreted protein and cytosolic protein may be natural or following transfection of a vector encoding the protein. Recombinant expression of the leaderless protein is preferred. Any of the leaderless proteins described above, chimeric leaderless proteins (i.e., fusion of leaderless protein with another protein or protein fragment), or protein sequences engineered to lack a leader sequence may be used. Secreted proteins that are exported by virtue of a leader sequence are well known and include, human chorionic gonadatropin (HCG$\alpha$) (SEQ ID NO:3), growth hormone, hepatocyte growth factor, transferrin, nerve growth factor, vascular endothelial growth factor, ovalbumin, and insulin-like growth factor. Similarly, cytosolic proteins are well known and include, neomycin, $\beta$-galactosidase, actin and other cytoskeletal proteins, enzymes, such as protein kinase A or C. The most useful cytosolic or secreted proteins are those that are readily measured in a convenient assay, such as ELISA. The three proteins may be co-expressed naturally or by transfection in the test cells, or transfected separately into host cells.

Merely by way of example, a construct containing the 18 kD isoform of FGF-2 is described. Plasmid 18 dx encodes the 18 kD isoform of FGF-2, which was derived from the wild-type human FGF-2 cDNA as previously described (Florkiewicz and Sommer, *Proc. Natl. Acad. Sci. USA* 86:3978, 1989). The FGF-2 sequence was truncated 11 bp 5' of the ATG codon for the 18 kD isoform. Thus, only the 18 kD form may be expressed. A fragment containing the cDNA was inserted into pJC119, an SV-40 based expression vector. It will be apparent that other expression vectors may be interchangeably used and that the choice of the vector will depend in part upon the host cell to be transfected. FGF-2 cDNA was expressed in COS cells using an SV40-based expression vector. The vector, pJC119 (Sprague et al., *J. Virol.* 45:773, 1983), is an SV-40 based vector, which uses the SV-40 late promoter to control expression of the inserted gene. COS cells were chosen because they normally express very low levels of FGF-2 and, as such, possess the appropriate cellular machinery for export of this leaderless protein.

Other leaderless proteins described above may be used in constructs in place of FGF-2. DNA molecules encoding these proteins may be obtained by conventional methods, such as library screening, PCR amplification and cloning, or obtained from the ATCC/NTH repository of human and mouse DNA probes. Nucleotide sequences of these proteins are generally available from Genbank, and EMBL databases or publications.

It will be recognized that other cell types, vectors, promotors, and other elements used for expression may be readily substituted according to well known principals. At minimum, a vector construct containing the leaderless protein must have a promoter sequence that is active in the target cell. Optionally, and preferably, the construct contains an enhancer, a transcription terminator, and a selectable marker. Such vectors are chosen to be suitable for the species or tissue type of the transfected cell. The cell may be mammalian, avian, or other eukaryotic cell, including yeast, in origin.

Mammalian cells suitable for carrying out the present invention include, amongst others, COS (ATCC No. CRL 1650), BHK (ATCC No. CRL 6281), CHO (ATCC No. CCL 61), HeLa (ATCC No. CCL2), 293 (ATCC No. 1573), NS-1 (ATCC No. T1B18), and Hep G2 (ATCC No. HB 8065).

A wide variety of promoters may be used within the context of the present invention. The choice of promoter will depend, at least in part, on the recipient cell line for transfection. By way of examples, promoters such as the SV40 promoter described above, MoMuLV LTR, RSV LTR, adenoviral promoter, metallothionein gene promoter, cytomegalovirus immediate early promoter or late promoter may be used. A tissue specific promoter may also be used, as long as it is activated in the target cell. For example, the immunoglobulin promoter can be used to express genes in B lymphocytes. Preferred promoters express the leaderless protein at high levels.

Assays to detect leaderless protein, secreted protein, and cytosolic protein include immunoprecipitation of proteins labeled in a pulse-chase procedure, ELISA, Western Blot, biological assays, and phagokinetic tracts. In all these assays, test cells expressing and exporting a leaderless protein are incubated with and without the candidate inhibitor.

Immunoprecipitation is a preferred assay to determine inhibition. Briefly, for immunoprecipitation, cells expressing a leaderless protein from an introduced vector construct, are labeled with $^{35}$S-methionine or $^{35}$S-cystein for a brief period of time, typically 15 minutes, in methionine- and cystein-free cell culture medium. Following pulse-labeling, cells are washed with medium supplemented with excess unlabeled methionine and cysteine plus heparin if the leaderless protein is heparin-binding. Cells are then cultured in the same chase medium for various periods of time. Candidate inhibitors are added to cultures at various concentration. Culture supernatant is collected and clarified. Supernatants are incubated with anti-FGF-2 immune serum or a monoclonal antibody, followed by a developing reagent such as *Staphylococcus aureus* Cowan strain I, protein A Sepharose®, or Gamma-bind™ G-Sepharose®. Immune complexes are pelleted by centrifugation, washed in a buffer containing 1% NP-40 and 0.5% deoxycholate, EGTA, PMSF, aprotinin, leupeptin, and pepstatin. Precipitates are then washed in a buffer containing sodium phosphate, pH 7.2, deoxycholate, NP-40, and SDS. Immune complexes are eluted into an SDS gel sample buffer and separated by SDS-PAGE. The gel is processed for fluorgraphy, dried and exposed to x-ray film.

Alternatively, and ELISA is used to detect and quantify the amount of FGF-2 or other leaderless protein in cell supernatants. Briefly, when FGF-2 is the test leaderless protein, 96-well plates are coated with an anti-FGF-2 antibody, washed, and supernatant is added to the wells. Following incubation and washing, a second antibody to FGF-2 is added. Following further incubation, a developing reagent is added and the amount of FGF-2 determined using an ELISA plate reader. The developing reagent is typically an anti-isotype antibody coupled with an enzyme, such as horseradish peroxidase, which acts upon a substrate resulting in a colorimetric reaction. It will be recognized that rather than using a second antibody coupled to an enzyme, the anti-FGF-2 antibody may be directly coupled to the horseradish peroxidase, or other equivalent detection reagent. If necessary, cell supernatants may be concentrated to raise the detection level.

Alternatively, concentrated supernatant may be electrophoresed on an SDS-PAGE gel and transferred to a solid support, such as nylon or nitrocellulose. The leaderless protein is then detected by an immunoblot (Harlow, *Antibodies: A Laboratory Manual*, Cold Spring Harbor Laboratory, 1988), using an antibody to the leaderless protein containing an isotopic or non-isotopic reporter group. These reporter groups include, but are not limited to enzymes, cofactors, dyes, radioisotopes, luminescent molecules, fluorescent molecules and biotin. Preferably, the reporter group is $^{125}$I or horseradish peroxidase, which may be detected by incubation with 2,2'-azino-di-3-ethylbenzthiazoline sulfonic acid.

An alternative assay, a bioassay, may be performed to quantify the amount of the leaderless protein exported into a cell medium. For example, the bioactivity of the 18 kD FGF-2 may be measured by a proliferation assay, such as the incorporation of tritiated thymidine. Briefly, cells transfected with an expression vector containing FGF-2 are cultured for approximately 30 hours, during which time a candidate inhibitor is added. Following incubation, cells are transferred to a low serum medium for a further 16 hours of incubation. The medium is removed and clarified by centrifugation. A lysis buffer containing protease inhibitors is added. FGF-2 is enriched by binding to heparin-Sepharose® CL-6B and eluted with 3.0 M NaCl, after non-FGF-2 proteins are eluted with 1.0M NaCl. Bioactivity of the FGF-2 is then measured by adding various amounts of the eluate to cultured quiescent 3T3 cells. Tritiated thymidine is added to the medium and TCA precipitable counts are measured approximately 24 hours later. For a standard, purified recombinant human FGF-2 may be used.

For leaderless proteins, that cause cell motility, such as FGF-2, a phagokinetic tract assay may be used to determine the amount of leaderless protein exported (Mignatti et al., *J. Cellular Physiol.* 151:81–93, 1992). In this assay, cells are allowed to migrate and microscope cover slip coated with colloidal gold. Under dark field illumination, the gold particles appear as a homogenous layer of highly refringent particles on a dark background. When a cell migrates on the substrate, it pushes aside the gold particles producing a dark track. An image analyzer may be used to measure the length of the tracks. Under conditions cell motility directly correlates with the amount of FGF-2 produced by the cells. The choice of the bioassay will depend, at least in part, by the leaderless protein tested.

In any of these assays, a cardiac glycoside or aglycone derivative inhibits export if there is a statistically significant reduction in the amount of protein detected extracellularly in the assay performed with the inhibitor compared to the assay performed without the inhibitor. Preferably, the inhibitor reduces export of the leaderless protein by at least 50%, even more preferably 80% or greater, and also preferably, in a dose-dependent manner. In addition, there should be no statistically significant effect on the appearance of either the secreted protein or the cytosolic protein. Preferably, there is less than a 10% increase or decrease in the appearance of these two proteins.

Administration

As described above, an inhibitor of the export of a leaderless protein is useful for treating tumors, inhibiting proliferation of cells, including smooth muscle cells that cause restenosis, and treating complications of diabetes, among other uses. Treatment means that symptoms may be lessened or the progression of the disease or conditions halted or delayed. Cells to be treated are contacted with a cardiac glycoside or aglycone derivative of a cardiac glycoside at a therapeutically effective dosage. Contacting may be effected by incubation of cells ex vivo or in vivo, such as by topical treatment, delivery by specific carrier or by vascular supply.

The conjugates herein may be formulated into pharmaceutical compositions suitable for topical, local, intravenous and systemic application. Time release formulations are also desirable. Effective concentrations of one or more of the conjugates are mixed with a suitable pharmaceutical carrier or vehicle. The concentrations or amounts of the conjugates that are effective requires delivery of an amount, upon administration, that ameliorates the symptoms or treats the disease. Typically, the compositions are formulated for single dosage administration. Therapeutically effective concentrations and amounts may be determined empirically by testing the conjugates in known in vitro and in vivo systems, such as those described herein; dosages for humans or other animals may then be extrapolated therefrom.

Candidate tumors for treatment as described herein include those with receptors for FGF. Such tumors include melanomas, teratocarcinomas, ovarian carcinomas, bladder tumors, and neuroblastomas.

Other disease, disorders, and syndromes are suitable for treatment. Diabetic complications, such as diabetic retinopathy, restenosis, polycystic kidney disease, and atherosclerosis are also candidates for such treatments. Cells in the eye, kidney and peripheral nerve, which are effected in diabetes, may be treated with the conjugates described herein.

Pharmaceutical carriers or vehicles suitable for administration of the conjugates provided herein include any such carriers known to those skilled in the art to be suitable for the particular mode of administration. In addition, the inhibitor may be formulated as the sole pharmaceutically active ingredient in the composition or may be combined with other active ingredients.

The compositions of the present invention may be prepared for administration by a variety of different routes. Local administration of the cardiac glycosides or aglycone derivatives is preferred. The inhibitor may be mixed with suitable excipients, such as salts, buffers, stabilizers, and the like. If applied topically, such as to the skin and mucous membranes, the inhibitor may be in the form of gels, creams, and lotions. Such solutions, particularly those intended for ophthalmic use, may be formulated as 0.01%–10% isotonic solutions, pH about 5–7, with appropriate salts (see, e.g., U.S. Pat. No. 5,116,868).

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbin acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. There may be prepared according to methods known to those skilled in the art.

The inhibitor may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydides, polyglycoli acid, polyorthoesters, polylactic acid and others. For example, the compositions may be applied during surgery using a sponge, such as a commercially available surgical sponge (see, e.g., U.S. Pat. Nos. 3,956,044 and 4,045,238).

The inhibitors can be administered by any appropriate route, for example, orally, parenterally, intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors and restenosis will typically be treated by systemic, intradermal or intramuscular modes of administration.

The inhibitor is included in the pharmaceutically acceptable carrier in an amount sufficient to exert a therapeutically useful effect in the absence of undesirable side effects. It is understood that number and degree of side effects depends upon the condition for which the conjugates are administered. For example, certain toxic and undesirable side effects are tolerated when treating life-threatening illnesses, such as tumors, that would not be tolerated when treating disorders of lesser consequence. The concentration of conjugate in the composition will depend on absorption, inactivation and excretion rates thereof, the dosage schedule, and amount administered as well as other factors known to those of skill in the art.

The inhibitor may be administered one time, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The following examples are offered by way of illustration and not by way of limitation.

EXAMPLE 1

Construction of Plasmid Expressing FGF-2

The expression vector containing the 18 kD isoform of FGF-2 was constructed as follows. The sequence of the 18 kD isoform of human FGF-2 was provided by plasmid 18 dx (Florkiewicz and Sommer, *Proc. Natl. Acad. Sci. USA* 86:3978–3981, 1989). This vector only expresses the 18 kD isoform because the sequences upstream of the ApaI site located 11 bp 5' of the ATG codon initiating translation of the 18 kD FGF-2 isoform were deleted. Briefly, plasmid p18ds was linearized with ApaI and an oligonucleotide adaptor containing an XhoI site was ligated to the plasmid. The XhoI restriction fragment containing FGF-2 was purified and subloned into the XhoI site of pJC119 (Sprague et al., supra).

An expression vector encoding hCG-alpha was provided by Dr. Carolyn Machamer (Dept. of Cell Biology, Johns Hopkins Medical School) and is identical to Guan et al., (J. Biol. chem. 263:5306–5313, 1988).

EXAMPLE 2

Cell Culture, Transfection, and Metabolic Labeling

COS-1 cells obtained from the American Type Culture Collection (ATCC CRL 1650) are cultured in DMEM supplemented with 10% fetal bovine serum, 2 mM L-glutamine, 1 mM sodium pyruvate, 100 U/mL penicillin, and 100 U/mL streptomycin. COS-1 cells are transfected with 10 $\mu$g of CsCl-purified plasmid DNA in 1 ml of transfection buffer (140 mM NaCl, 3 mM KCl, 1 mM CaCl$_2$, 0.5 mM MgCl$_2$, 0.9 mM Na$_2$HPO$_4$, 25 mM Tris, pH 7.4. The plasmid 18 ds was co-transfected with pMAMneo (Clontech, Palo Alto, Calif.), which contains the selectable marker neomycin phosphotransferase. When 2 $\mu$g of p18dx was co-transfected with 10 $\mu$g of pMAMneo, greater than 70% of transfected cells expressed both FGF-2 and neo, as determined by immunofluorescence microscopy.

At 40 to 48 hours post-DNA transfection, COS-1 cells were metabolically pulse-labelled for 15 min with 100 $\mu$Ci of $^{35}$S-methionine and $^{35}$S-cysteine (Trans $^{35}$S-label, ICN Biomedicals, Irvine, Calif.) in 1 ml of met and cysteine free DMEM. Following labeling, the cell monolayers were washed once with DMEM supplemented with excess (10 MM) unlabeled methionine and cysteine plus 25 $\mu$g/ml heparin. Cells were then cultured in 2 ml of this medium for the indicated lengths of time. For the indicated cultures, chase medium was supplemented with ouabain at the indicated concentrations.

EXAMPLE 3

Immunoprecipitation and Western Blot Analysis

Cell and conditioned medium fractions are prepared for immunoprecipitation essentially as described previously (Florkiewicz et al., *Growth Factors* 4:265–275, 1991; Fiorkiewicz et al., *Ann. N.Y. Acad. Sci.* 638:109–126) except that 400 $\mu$l of lysis buffer (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) was added to the medium fraction after clarification by centrifugation in a microfuge for 15 min. Cell or medium fractions are incubated with guinea pig anti-FGF-2 immune serum (1:200) at 21° C. for 40 min. GammaBind™ G Sepharose® (Pharmacia LKB Biotechnology, Uppsala, Sweden) was added for an additional 30 min incubation. Immune complexes were pelleted by microfuge centrifugation, washed three times with lysis buffer and four times with ice cold Immunoprecipitation wash buffer (0.15M NaCl, 0.01 M Na-phosphate pH 7.2, 1% deoxycholate, 1% NP-40, 0.1% sodium dodecyl sulfate). Immune complexes were eluted into SDS gel sample buffer 125 mM Tres, pH 6.8, 4% SDS, 10% glycerol, 0.004% bromphenol blue, 2 mM EGTA and separated by 12% SDS-PAGE. The gel was processed for fluorography, dried, and exposed to X-ray film at −70° C. When neomycin phosphotransferase was immunoprecipitated, a rabbit anti-NPT antibody (5 Prime-3 Prime, Boulder, Colo.) was used.

For Western blot analysis, proteins were transferred from the 12% SDS-PAGE gel to a nitrocellulose membrane (pore size 0.45 $\mu$m in cold buffer containing 25 mM 3-[dimethyl (hydroxymethyl)methylamino]-2-hydroxypropane-sulfonic acid, pH 9.5, 20% methanol for 90 min at 0.4 amps. Membranes were blocked in 10 mM Tris, pH7.5, 150 mM NaCl, 5 mM NaN$_3$, 0.35% polyoxyethylene-sorbitan monolaurate, and 5% nonfat dry milk (Carnation Co., Los Angeles, Calif.) for 1 hr at room temperature. Membranes were incubated with a monoclonal anti-FGF-2 antibody (Transduction Laboratories, Lexington, Ky.) at 0.3 $\mu$g/ml in blocking buffer at 4° C. for 16 hr. Following incubation, membranes were washed at room temperature with 10 changes of buffer containing 150 mM NaCl, 500 mM sodium phosphate pH 7.4, 5 mM NaN$_3$, and 0.05% polyoxyethylene-sorbitan monolaurate. Membranes were then incubated in blocking buffer containing 1 $\mu$g/ml rabbit anti-mouse IgG (H+L, affinipure, Jackson Immuno Research Laboratories, West Grove, Pa.) for 30 min at room temperature. Membranes were subsequently washed in 1 l of buffer described above, and incubated for 1 hr in 100 ml of blocking buffer containing 15 $\mu$Ci $^{125}$I-protein A (ICN Biochemicals, Costa Mesa, Calif.), and washed with 1 l of buffer. The radiosignal was visualized by autoradiography.

EXAMPLE 4

FGF-2 Bioassay

The bioactivity of FGF-2 may be measured in a thymidine incorporation assay. Cells transfected with FGF-2 as described above are incubated for 30 hr. At this time, the culture medium is replaced with 6 ml of DMEM containing 0.5% FBS (low serum medium) for 16 hr. The medium is removed, clarified by centrifugation in a microfuge for 15 min at 4° C. An equal volume of lysis buffer and heparin-Sepharose® CL-6B is added and the mixture incubated with rocking for 2 hr at 4° C. The Sepharose is pelleted and washed three times with lysis buffer followed by three washes with HS-wash buffer (20 mM Tris, pH 7.4, 5 mM EDTA, 2 mM EGTA, plus protease inhibitors, 0.5 M NaCl) and washed three times with HS-wash buffer containing 1 M NaCl. Proteins that remained bound to the Sepharose were eluted into HS wash buffer containing 3 M NaCl.

The stimulation of DNA synthesis was measured in quiescent Swiss 3T3 cells (clone NR-6) as previously described (Witte et al., *J. Cell Physiol.* 137:86–94, 1988; Florkiewicz and Sommer *Proc. Natl. Acad. Sci. USA* 86:3978–3981, 1989). Briefly, cells were plated at low density and growth arrested by culturing for 72 hr in 1 ml of media containing 0.1% FBS. Various amounts of the 3 M NaCl HS-eluate are added directly to the culture medium and the level of [$^3$H]-thymidine incorporation into TCA precipitable counts was measured 20–24 hr later. As a control, 1 pg to 1 ng of recombinant human FGF-2 was added to the cells in a similar manner.

EXAMPLE 5

Brefeldin-Resistant Export of FGF-2

Brefeldin A inhibits secretion of proteins from the ER and Golgi. In contrast, export of a leaderless protein is not inhibited by treatment with Brefeldin A.

COS-1 cells are obtained from the American Type Culture Collection and cultured in Dulbecco's Modified Eagle Medium (DMEM, University of California San Diego Core Facility) supplemented with 10% fetal bovine serum (Gemini Bioproducts, Inc.), 2 mM L-glutamine, 1 mM sodium pyruvate, 0.1 mM non-essential amino acids, 100 units/ml penicillin, and 100 units/ml streptomycin. The plasmid SV-40-based expression vector containing the wild type (human) cDNA-encoding multiple FGF-2 isoforms (24, 23, 22 and 18-kD) has been described previously (Florkiewica and Sommer, supra). Approximately $3 \times 10^3$ COS-1 cells in a 60 mm tissue culture dish are transfected with 10 μg of CsCl-purified plasmid DNA mixed with 1.0 ml of transfection buffer (140 mM NaCl. 3 mM KCl. 1 mM $CaCl_2$, 0.5 mM $MgCl_2$, 0.9 mM $Na_2HPO_4$, 25 mM Tris pH 7.4; all from Sigma Chemical Company). Under these co-transfection conditions using 2 μg of p18dx plug 10 μg pMAMneo, greater than 70% of transfected cells express both proteins, as determined by immunofluorescence microscopy. The ratio of plasmid DNA may be varied with insignificant change in results. Forty to 48 hours post-DNA transfection COS-1 cells are metabolically pulse-labeled for 15 minutes with 100 μCi of $^{35}$S-methionine and $^{35}$cysteine (Trans$^{35}$S-label, ICN Biomedicals, Inc.) in 1.0 ml of methionine-and cysteine-free DMEM. After pulse-labeling, the cell monolayers are washed once with DMEM supplemented with excess (10 mM) unlabeled methionine (Sigma Chemical Company) and cystine (Sigma Chemical Company) and then cultured in 1.0 ml of the same medium (chase) for the indicate lengths of time. Cultures treated with Brefeldin A include 15 μg/ml of Brefeldin A in the chase medium. Chase medium is also supplemented with 25 μg/ml heparin (Sigma Chemical Company). Although heparin is not necessary to qualitatively detect FGF-2 export, it is necessary in order to quantitively detect the export of FGF-2 in this assay.

Cell and medium fractions are prepared for immunoprecipitation essentially as described previously (Florkiewica et al., 1991) except that 400 μl of lysis buffer without NaCl (1% NP-40, 0.5% deoxycholate. 20 Tris pH 7.5, 5 mM EDTA, 2 mM EGTA, 0.01 mM phenylmethylsufonyl fluoride, 10 ng/ml aprotinin, 10 ng/ml leupeptin, and 10 ng/ml pepstatin) is added to the medium fraction clarified by microfuge centrifugation for 15 minutes at 4° C. before adding immune serum. Both cell and medium fractions are incubated with a 1:200 dilution of guinea pig anti-FGF-2 immune serum (prepared in our laboratory) at 21° C. for 40 minutes and then GammaBind G Sepharose® (Pharmacia LKB Biotechnology) is added for an additional 30 minutes incubation. G-Sepharose-bound immune complexes are pelleted, washed three times with lysis buffer and four times with ice cold immunoprecipitation wash buffer (0.15 M NaCl, 0.01 M Na-Phosphate pH 7.2, 1% deoxycholate, 1% NP-40, 0.1% sodium dodecyl sulfate). Immune complexes are eluted directly into SDS-gel-sample buffer and separated by 12% SDS-polyacylamide gel electrophoresis (PAGE). The gel is processed for fluorography, dried and exposed to X-ray film at −70° C. For immunoprecipitations involving neomycin phosphotransferase (NPT), rabbit anti-NPT antibody (5 Prime-3 Prime, Inc., Boulder, Colo.) was used.

Figures 5A, 5B, 5C:
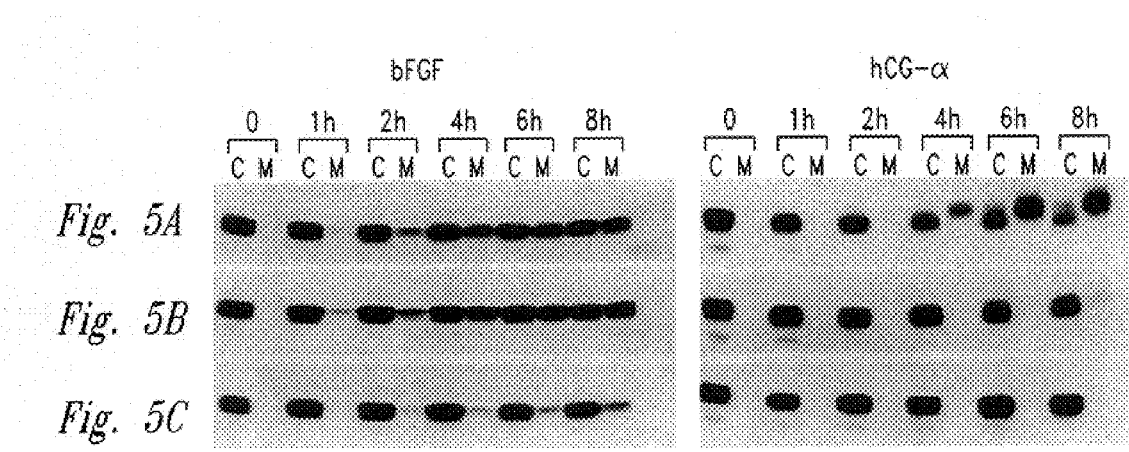
FIG. 5 is a photograph of immunoprecipitated FGF-2 and HCG-α from cellular (C) and medium (M) fractions following metabolic labeling. COS-1 cells were transfected with P18dx or hCG-α and metabolically labeled in medium alone (A), Brefedin A (B) or 2-deoxy-D-glucose plus NaN₃ (C). FGF-2 and HCG-α were immunopreciptated from cells (C) or medium (M), electrophoresed and autoradiographed.

As shown in FIG. 5, the export of 18 kD FGF-2 is brefeldin A-resistant and is energy dependent. Sample A was chased with medium alone, sample B was chased with medium supplemented with 25 μg/ml Brefeldin A and sample C was chased with medium supplemented with 50 mM 2-deoxy-D-glucose and $NaN_3$. As shown in FIG. 5, FGF-2 is exported to the medium by 2 hours. Brefeldin A had no substantial effect on this export. However, when $NaN_3$, a metabolic inhibitor, is present, export is substantially reduced. In contrast, hCG-α is secreted into the medium by 4 hours and is brefeldin sensitive and energy dependent. hCG-α contains a hydrophobic leader (signal) sequence and as a consequence is secreted via the ER and Golgi.

EXAMPLE 6

Inhibition of Leaderless Proteins

COS cells are co-transfected as described above with plasmids expressing FGF2, hCG-α or neomycin. Metabolic labeling is performed as described above, except that during the chase period, inhibitor is added at 10 nM to 1 mM in log increments. At the end of the chase, cells and cell media are harvested and processed for immune precipitations as described above.

Figure 2A:
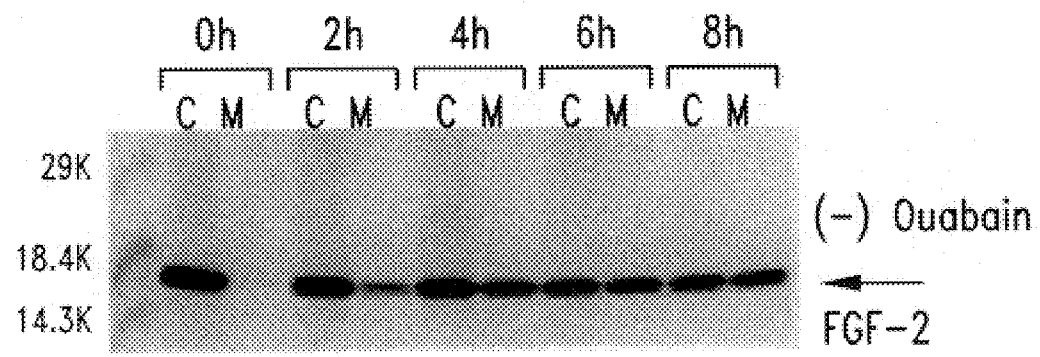
FIG. 2 is an SDS-PAGE gel of pulse-labeled, immunoprecipated cellular (lanes marked C) and extracellular FGF-2 (lanes marked M) following treatment without ouabain (panel A) and ouabain (panel B).
Figure 2B:
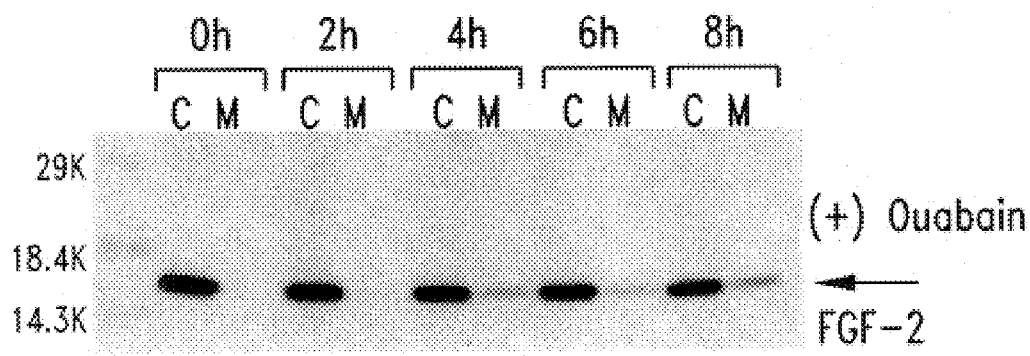
Figure 3A:
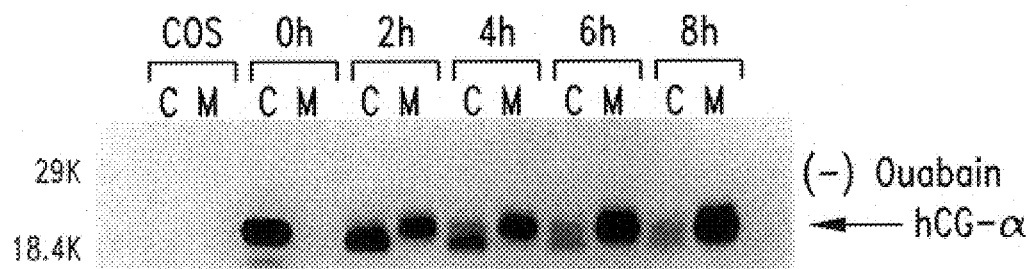
FIG. 3 is an SDS-PAGE gel of pulse-labeled, immunoprecipitated cellular (lanes marked C) and extracellular (lanes marked M) human corionic gonadatrophin α following treatment without oubain (panel A) and with ouabain (panel B).
Figure 3B:
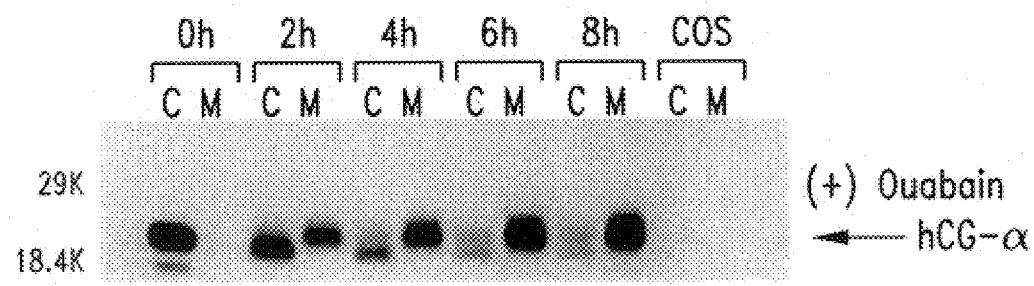
Figure 4:
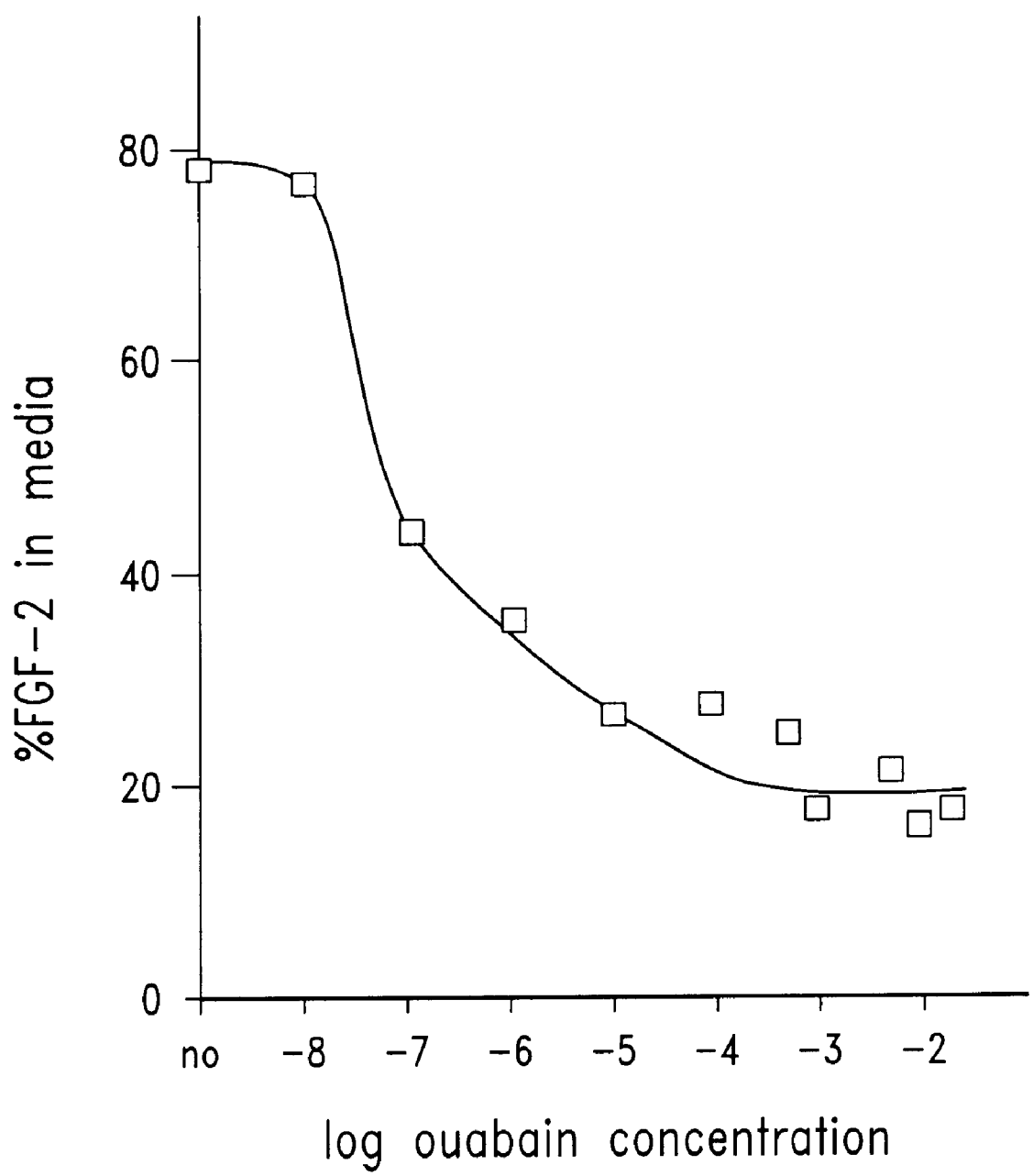
FIG. 4 is a graph showing the quantitation of FGF-2 export following treatment with ouabain.

Ouabain and digoxin inhibited the export of FGF-2, but not human chorionic gonadatrophin α. Ouabain inhibited 50% of export at approximately 0.1 μM and digoin at approximately 5 μM. Further experiments with ouabain demonstrate that inhibition is time-dependent (FIG. 2), does not affect secretion of hCG-α (FIG. 3) and inhibits export of FGF-2 in a dose-dependent manner (FIG. 4).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating complications of diabetes, comprising contacting a cell exporting FGF or other leaderless protein with a therapeutically effective amount of a cardiac glycoside.

2. The method of claim 1 wherein the cardiac glycoside is selected from the group consisting of digoxin, strophanthin K, digitoxin, lanatoside A, ouabain, digitoxose, gitoxin, oleandrin and acovenoside A.

3. The method of claim 1 wherein the cardiac glycoside is ouabain.

4. The method of claim 1 wherein the cardiac glycoside is digoxin.

5. A method of treating complications of diabetes, comprising contacting a cell exporting FGF or other leaderless protein with a therapeutically effective amount of an aglycone derivative of a cardiac glycoside.

6. The method of claim 5 wherein the aglycone is selected from the group consisting of digoxigenin, digitoxigenin, and uzarigenin.

7. The method of claim 5 wherein the aglycone derivative is digoxigenin.

\* \* \* \* \*

UNITED STATES PATENT AND TRADEMARK OFFICE
CERTIFICATE OF CORRECTION

PATENT NO. : 6,281,197 B1
DATED : August 28, 2001
INVENTOR(S) : Robert Z. Florkiewicz Page 1 of 1

It is certified that error appears in the above-identified patent and that said Letters Patent is hereby corrected as shown below:

<u>Column 1,</u>
Line 16, insert -- This invention was made with government support under Grant No. DK 18811 by the National Institutes of Health. The Government has certain rights in the invention. --

Signed and Sealed this

Twenty-first Day of May, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 3877 base pairs
      (B) TYPE: nucleic acid
      (C) STRANDEDNESS: single
      (D) TOPOLOGY: linear -continued (xi) SEQUENCE DESCRIPTION: SEQ ID NO: 1:

```
GCCAGATTAG CGGACGCGTG CCCGCGGTTG CAACGGGATC CCGGGCGCTG CAGCTTGGGA      60

GGCGGCTCTC CCCAGGCGGC GTCCGCGGAG ACAACCATCC GTGAACCCCA GGTCCCGGCG     120

CGCCGGCTCG CCGCGCACCA GGGGCCGGCG GACAGAAGAG CGGCCGAGCG GCTCGAGGCT     180

GGGGGACCCG GCGCGGCCGC GCGCTGCCGG GCGGGAGGCT GGGGGGCCGG GGCGGGGCCG     240

TGCCCCGGAG CGGGTCGGAG GCCGGGGCCG GGGCCGGGGG ACGGCGGCTC CCCGCGCGGC     300

TCCAGCGGCT CGGGGATCCC GGCCGGGCCC CGCAGGACCA TGGCAGCCGG GAGCATCACC     360

ACGCTGCCCG CCTTGCCCGA GGATGGCGGC AGCGGCGCCT TCCCGCCCGG CCACTTCAAG     420

GACCCCAAGC GGCTGTACTG CAAAAACGGG GGCTTCTTCC TGCGCATCCA CCCCGACGGC     480

CGAGTTGACG GGGTCCGGGA GAAGAGCGAC CCTCACATCA AGCTACAACT TCAAGCAGAA     540

GAGAGAGGAG TTGTGTCTAT CAAAGGAGTG TGTGCTAACC GTTACCTGGC TATGAAGGAA     600

GATGGAAGAT TACTGGCTTC TAAATGTGTT ACGGATGAGT GTTTCTTTTT TGAACGATTG     660

GAATCTAATA ACTACAATAC TTACCGGTCA AGGAAATACA CCAGTTGGTA TGTGGCACTG     720

AAACGAACTG GCAGTATAAA ACTTGGATCC AAAACAGGAC CTGGGCAGAA AGCTATACTT     780

TTTCTTCCAA TGTCTGCTAA GAGCTGATTT TAATGGCCAC ATCTAATCTC ATTTCACATG     840

AAAGAAGAAG TATATTTTAG AAATTTGTTA ATGAGAGTAA AAGAAAATAA ATGTGTAAAG     900

CTCAGTTTGG ATAATTGGTC AAACAATTTT TTATCCAGTA GTAAAATATG TAACCATTGT     960

CCCAGTAAAG AAAAATAACA AAAGTTGTAA AATGTATATT CTCCCTTTTA TATTGCATCT    1020

GCTGTTACCC AGTGAAGCTT ACCTAGAGCA ATGATCTTTT TCACGCATTT GCTTTATTCG    1080

AAAAGAGGCT TTTAAAATGT GCATGTTTAG AAACAAAATT TCTTCATGGA AATCATCATA    1140

TACATTAGAA AATCACAGTC AGATGTTTAA TCAATCCAAA ATGTCCACTA TTTCTTATGT    1200

CATTCGTTAG TCTACATGTT TCTAAACATA TAAATGTGAA TTTAATCAAT TCCTTTCATA    1260

GTTTTATAAT TCTCTGGCAG TTCCTTATGA TAGAGTTTAT AAAACAGTCC TGTGTAAACT    1320

GCTGGAAGTT CTTCCACAGT CAGGTCAATT TTGTCAAACC CTTCTCTGTA CCCATACAGC    1380

AGCAGCCTAG CAACTCTGCT GGTGATGGGA GTTGTATTTT CAGTCTTCGC CAGGTCATTG    1440

AGATCCATCC ACTCACATCT TAAGCATTCT TCCTGGCAAA AATTTATGGT GAATGAATAT    1500

GGCTTTAGGC GGCAGATGAT ATACATATCT GACTTCCCAA AAGCTCCAGG ATTTGTGTGC    1560

TGTTGCCGAA TACTCAGGAC GGACCTGAAT TCTGATTTTA TACCAGTCTC TTCAAAACCT    1620

TCTCGAACCG CTGTGTCTCC TACGTAAAAA AAGAGATGTA CAAATCAATA ATAATTACAC    1680

TTTTAGAAAC TGTATCATCA AAGATTTTCA GTTAAAGTAG CATTATGTAA AGGCTCAAAA    1740

CATTACCCTA ACAAAGTAAA GTTTTCAATA CAAATTCTTT GCCTTGTGGA TATCAAGAAA    1800

TCCCAAAATA TTTTCTTACC ACTGTAAATT CAAGAAGCTT TTGAAATGCT GAATATTTCT    1860

TTGGCTGCTA CTTGGAGGCT TATCTACCTG TACATTTTTG GGGTCAGCTC TTTTTAACTT    1920

CTTGCTGCTG TTTTTCCCAA AAGGTAAAAA TATAGATTGA AAAGTTAAAA CATTTTGCAT    1980

GGCTGCAGTT CCTTTGTTTC TTGAGATAAG ATTCCAAAGA ACTTAGATTT ATTTCTTCAA    2040

CACCGAAATG CTGGAGGTGT TTGATCAGTT TTCAAGAAAC TTGGAATATA AATAATTTTA    2100

TAATTCAACA AAGGTTTTCA CATTTTATAA GGTTGATTTT TCAATTAAAT GCAAATTTAT    2160

GTGGCAGGAT TTTTATTGCC ATTAACATAT TTTTGTGGCT GCTTTTTCTA CACATCCAGA    2220

TGGTCCCTCT AACTGGGCTT TCTCTAATTT TGTGATGTTC TGTCATTGTC TCCCAAAGTA    2280

TTTAGGAGAA GCCCTTTAAA AAGCTGCCTT CCTCTACCAC TTTGCTGAAA GCTTCACAAT    2340
```

-continued

```
TGTCACAGAC AAAGATTTTT GTTCCAATAC TCGTTTTGCC TCTATTTTAC TTGTTTGTCA    2400

AATAGTAAAT GATATTTGCC CTTGCAGTAA TTCTACTGGT GAAAAACATG CAAAGAAGAG    2460

GAAGTCACAG AAACATGTCT CAATTCCCAT GTGCTGTGAC TGTAGACTGT CTTACCATAG    2520

ACTGTCTTAC CCATCCCCTG GATATGCTCT TGTTTTTTCC CTCTAATAGC TATGGAAAGA    2580

TGCATAGAAA GAGTATAATG TTTTAAAACA TAAGGCATTC GTCTGCCATT TTCAATTAC     2640

ATGCTGACTT CCCTTACAAT TGAGATTTGC CCATAGGTTA AACATGGTTA GAAACAACTG    2700

AAAGCATAAA AGAAAAATCT AGGCCGGGTG CAGTGGCTCA TGCCCATATT CCCTGCACTT    2760

TGGGAGGCCA AGCAGGAGG  ATCGCTTGAG CCCAGGAGTT CAAGACCAAC CTGGTGAAAC    2820

CCCGTCTCTA CAAAAAAACA CAAAAAATAG CCAGGCATGG TGGCGTGTAC ATGTGGTCTC    2880

AGATACTTGG GAGGCTGAGG TGGGAGGGTT GATCACTTGA GGCTGAGAGG TCAAGGTTAC    2940

AGTGAGCCAT AATCGTGCCA CTGCAGTCCA GCCTAGGCAA CAGAGTGAGA CTTTGTCTCA    3000

AAAAAAGAGA AATTTTCCTT AATAAGAAAA GTAATTTTTA CTCTGATGTG CAATACATTT    3060

GTTATTAAAT TTATTATTTA AGATGGTAGC ACTAGTCTTA AATTGTATAA AATATCCCCT    3120

AACATGTTTA AATGTCCATT TTTATTCATT ATGCTTTGAA AAATAATTAT GGGGAAATAC    3180

ATGTTTGTTA TTAAATTTAT TATTAAAGAT AGTAGCACTA GTCTTAAATT TGATATAACA    3240

TCTCCTAACT TGTTTAAATG TCCATTTTTA TTCTTTATGT TTGAAAATAA ATTATGGGGA    3300

TCCTATTTAG CTCTTAGTAC CACTAATCAA AAGTTCGGCA TGTAGCTCAT GATCTATGCT    3360

GTTTCTATGT CGTGGAAGCA CCGGATGGGG GTAGTGAGCA AATCTGCCCT GCTCAGCAGT    3420

CACCATAGCA GCTGACTGAA AATCAGCACT GCCTGAGTAG TTTTGATCAG TTTAACTTGA    3480

ATCACTAACT GACTGAAAAT TGAATGGGCA AATAAGTGCT TTTGTCTCCA GAGTATGCGG    3540

GAGACCCTTC CACCTCAAGA TGGATATTTC TTCCCCAAGG ATTTCAAGAT GAATTGAAAT    3600

TTTTAATCAA GATAGTGTGC TTTATTCTGT TGTATTTTTT ATTATTTTAA TATACTGTAA    3660

GCCAAACTGA ATAACATTT  GCTGTTTTAT AGGTTTGAAG ACATAGGAAA AACTAAGAGG    3720

TTTTATTTTT GTTTTTGCTG ATGAAGAGAT ATGTTTAAAT ACTGTTGTAT TGTTTTGTTT    3780

AGTTACAGGA CAATAATGAA ATGGAGTTTA TATTTGTTAT TTCTATTTTG TTATATTTAA    3840

TAATAGAATT AGATTGAAAT AAAATATAAT GGGAAAT                             3877
```

(2) INFORMATION FOR SEQ ID NO: 2:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..474

(xi) SEQUENCE DESCRIPTION: SEQ ID NO: 2:

```
CGC AGG ACC ATG GCA GCC GGG AGC ATC ACC ACG CTG CCC GCC TTG CCC     48
Arg Arg Thr Met Ala Ala Gly Ser Ile Thr Thr Leu Pro Ala Leu Pro
 1               5                  10                  15

GAG GAT GGC GGC AGC GGC GCC TTC CCG CCC GGC CAC TTC AAG GAC CCC     96
Glu Asp Gly Gly Ser Gly Ala Phe Pro Pro Gly His Phe Lys Asp Pro
            20                  25                  30

AAG CGG CTG TAC TGC AAA AAC GGG GGC TTC TTC CTG CGC ATC CAC CCC    144
Lys Arg Leu Tyr Cys Lys Asn Gly Gly Phe Phe Leu Arg Ile His Pro
        35                  40                  45
```

```
GAC GGC CGA GTT GAC GGG GTC CGG GAG AAG AGC GAC CCT CAC ATC AAG      192
Asp Gly Arg Val Asp Gly Val Arg Glu Lys Ser Asp Pro His Ile Lys
     50                  55                  60

CTA CAA CTT CAA GCA GAA GAG AGA GGA GTT GTG TCT ATC AAA GGA GTG      240
Leu Gln Leu Gln Ala Glu Glu Arg Gly Val Val Ser Ile Lys Gly Val
 65                  70                  75                  80

TGT GCT AAC CGT TAC CTG GCT ATG AAG GAA GAT GGA AGA TTA CTG GCT      288
Cys Ala Asn Arg Tyr Leu Ala Met Lys Glu Asp Gly Arg Leu Leu Ala
                 85                  90                  95

TCT AAA TGT GTT ACG GAT GAG TGT TTC TTT TTT GAA CGA TTG GAA TCT      336
Ser Lys Cys Val Thr Asp Glu Cys Phe Phe Phe Glu Arg Leu Glu Ser
            100                 105                 110

AAT AAC TAC AAT ACT TAC CGG TCA AGG AAA TAC ACC AGT TGG TAT GTG      384
Asn Asn Tyr Asn Thr Tyr Arg Ser Arg Lys Tyr Thr Ser Trp Tyr Val
        115                 120                 125

GCA CTG AAA CGA ACT GGG CAG TAT AAA CTT GGA TCC AAA ACA GGA CCT      432
Ala Leu Lys Arg Thr Gly Gln Tyr Lys Leu Gly Ser Lys Thr Gly Pro
    130                 135                 140

GGG CAG AAA GCT ATA CTT TTT CTT CCA ATG TCT GCT AAG AGC TGA          477
Gly Gln Lys Ala Ile Leu Phe Leu Pro Met Ser Ala Lys Ser
145                 150                 155
```

(2) INFORMATION FOR SEQ ID NO: 3:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 3:

```
Arg Arg Thr Met Ala Ala Gly Ser Ile Thr Thr Leu Pro Ala Leu Pro
 1               5                  10                  15

Glu Asp Gly Gly Ser Gly Ala Phe Pro Pro Gly His Phe Lys Asp Pro
                 20                  25                  30

Lys Arg Leu Tyr Cys Lys Asn Gly Gly Phe Phe Leu Arg Ile His Pro
             35                  40                  45

Asp Gly Arg Val Asp Gly Val Arg Glu Lys Ser Asp Pro His Ile Lys
         50                  55                  60

Leu Gln Leu Gln Ala Glu Glu Arg Gly Val Val Ser Ile Lys Gly Val
 65                  70                  75                  80

Cys Ala Asn Arg Tyr Leu Ala Met Lys Glu Asp Gly Arg Leu Leu Ala
                 85                  90                  95

Ser Lys Cys Val Thr Asp Glu Cys Phe Phe Phe Glu Arg Leu Glu Ser
            100                 105                 110

Asn Asn Tyr Asn Thr Tyr Arg Ser Arg Lys Tyr Thr Ser Trp Tyr Val
        115                 120                 125

Ala Leu Lys Arg Thr Gly Gln Tyr Lys Leu Gly Ser Lys Thr Gly Pro
    130                 135                 140

Gly Gln Lys Ala Ile Leu Phe Leu Pro Met Ser Ala Lys Ser
145                 150                 155
```

(2) INFORMATION FOR SEQ ID NO: 4:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ix) FEATURE:
 (A) NAME/KEY: CDS
 (B) LOCATION: 1..348

(xi) SEQUENCE DESCRIPTION: SEQ ID NO: 4:

```
ATG GAT TAC TAC AGA AAA TAT GCA GCT ATC TTT CTG GTC ACA TTG TCG       48
Met Asp Tyr Tyr Arg Lys Tyr Ala Ala Ile Phe Leu Val Thr Leu Ser
160             165                 170                 175

GTG TTT CTG CAT GTT CTC CAT TCC GCT CCT GAT GTG CAG GAT TGC CCA       96
Val Phe Leu His Val Leu His Ser Ala Pro Asp Val Gln Asp Cys Pro
                180                 185                 190

GAA TGC ACG CTA CAG GAA AAC CCA TTC TTC TCC CAG CCG GGT GCC CCA      144
Glu Cys Thr Leu Gln Glu Asn Pro Phe Phe Ser Gln Pro Gly Ala Pro
            195                 200                 205

ATA CTT CAG TGC ATG GGC TGC TGC TTC TCT AGA GCA TAT CCC ACT CCA      192
Ile Leu Gln Cys Met Gly Cys Cys Phe Ser Arg Ala Tyr Pro Thr Pro
        210                 215                 220

CTA AGG TCC AAG AAG ACG ATG TTG GTC CAA AAG AAC GTC ACC TCA GAG      240
Leu Arg Ser Lys Lys Thr Met Leu Val Gln Lys Asn Val Thr Ser Glu
225                 230                 235

TCC ACT TGC TGT GTA GCT AAA TCA TAT AAC AGG GTC ACA GTA ATG GGG      288
Ser Thr Cys Cys Val Ala Lys Ser Tyr Asn Arg Val Thr Val Met Gly
240                 245                 250                 255

GGT TTC AAA GTG GAG AAC CAC ACG GCG TGC CAC TGC AGT ACT TGT TAT      336
Gly Phe Lys Val Glu Asn His Thr Ala Cys His Cys Ser Thr Cys Tyr
                260                 265                 270

TAT CAC AAA TCT TAA                                                  351
Tyr His Lys Ser
            275
```

(2) INFORMATION FOR SEQ ID NO: 5:

(i) SEQUENCE CHARACTERISTICS:
  (A) LENGTH: 116 amino acids
  (B) TYPE: amino acid
  (D) TOPOLOGY: linear (ii) MOLECULE TYPE: protein (xi) SEQUENCE DESCRIPTION: SEQ ID NO: 5:

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```

(2) INFORMATION FOR SEQ ID NO: 6:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..813

(xi) SEQUENCE DESCRIPTION: SEQ ID NO: 6:

```
ATG GCC AAA GTT CCA GAC ATG TTT GAA GAC CTG AAG AAC TGT TAC AGT         48
Met Ala Lys Val Pro Asp Met Phe Glu Asp Leu Lys Asn Cys Tyr Ser
        120             125             130

GAA AAT GAA GAA GAC AGT TCC TCC ATT GAT CAT CTG TCT CTG AAT CAG         96
Glu Asn Glu Glu Asp Ser Ser Ser Ile Asp His Leu Ser Leu Asn Gln
135             140             145

AAA TCC TTC TAT CAT GTA AGC TAT GGC CCA CTC CAT GAA GGC TGC ATG        144
Lys Ser Phe Tyr His Val Ser Tyr Gly Pro Leu His Glu Gly Cys Met
150             155             160             165

GAT CAA TCT GTG TCT CTG AGT ATC TCT GAA ACC TCT AAA ACA TCC AAG        192
Asp Gln Ser Val Ser Leu Ser Ile Ser Glu Thr Ser Lys Thr Ser Lys
            170             175             180

CTT ACC TTC AAG GAG AGC ATG GTG GTA GTA GCA ACC AAC GGG AAG GTT        240
Leu Thr Phe Lys Glu Ser Met Val Val Val Ala Thr Asn Gly Lys Val
            185             190             195

CTG AAG AAG AGA CGG TTG AGT TTA AGC CAA TCC ATC ACT GAT GAT GAC        288
Leu Lys Lys Arg Arg Leu Ser Leu Ser Gln Ser Ile Thr Asp Asp Asp
            200             205             210

CTG GAG GCC ATC GCC AAT GAC TCA GAG GAA GAA ATC ATC AAG CCT AGG        336
Leu Glu Ala Ile Ala Asn Asp Ser Glu Glu Glu Ile Ile Lys Pro Arg
215             220             225

TCA GCA CCT TTT AGC TTC CTG AGC AAT GTG AAA TAC AAC TTT ATG AGG        384
Ser Ala Pro Phe Ser Phe Leu Ser Asn Val Lys Tyr Asn Phe Met Arg
230             235             240             245

ATC ATC AAA TAC GAA TTC ATC CTG AAT GAC GCC CTC AAT CAA AGT ATA        432
Ile Ile Lys Tyr Glu Phe Ile Leu Asn Asp Ala Leu Asn Gln Ser Ile
            250             255             260

ATT CGA GCC AAT GAT CAG TAC CTC ACG GCT GCT GCA TTA CAT AAT CTG        480
Ile Arg Ala Asn Asp Gln Tyr Leu Thr Ala Ala Ala Leu His Asn Leu
            265             270             275

GAT GAA GCA GTG AAA TTT GAC ATG GGT GCT TAT AAG TCA TCA AAG GAT        528
Asp Glu Ala Val Lys Phe Asp Met Gly Ala Tyr Lys Ser Ser Lys Asp
            280             285             290

GAT GCT AAA ATT ACC GTG ATT CTA AGA ATC TCA AAA ACT CAA TTG TAT        576
Asp Ala Lys Ile Thr Val Ile Leu Arg Ile Ser Lys Thr Gln Leu Tyr
295             300             305

GTG ACT GCC CAA GAT GAA GAC CAA CCA GTG CTG CTG AAG GAG ATG CCT        624
Val Thr Ala Gln Asp Glu Asp Gln Pro Val Leu Leu Lys Glu Met Pro
310             315             320             325

GAG ATA CCC AAA ACC ATC ACA GGT AGT GAG ACC AAC CTC CTC TTC TTC        672
Glu Ile Pro Lys Thr Ile Thr Gly Ser Glu Thr Asn Leu Leu Phe Phe
            330             335             340

TGG GAA ACT CAC GGC ACT AAG AAC TAT TTC ACA TCA GTT GCC CAT CCA        720
Trp Glu Thr His Gly Thr Lys Asn Tyr Phe Thr Ser Val Ala His Pro
            345             350             355

AAC TTG TTT ATT GCC ACA AAG CAA GAC TAC TGG GTG TGC TTG GCA GGG        768
Asn Leu Phe Ile Ala Thr Lys Gln Asp Tyr Trp Val Cys Leu Ala Gly
            360             365             370
```

```
GGG CCA CCC TCT ATC ACT GAC TTT CAG ATA CTG GAA AAC CAG GCG TAG         816
Gly Pro Pro Ser Ile Thr Asp Phe Gln Ile Leu Glu Asn Gln Ala
375                 380                 385
```

(2) INFORMATION FOR SEQ ID NO: 7:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp
                85                  90                  95

Leu Glu Ala Ile Ala Asn Asp Ser Glu Glu Ile Ile Lys Pro Arg
                100                 105                 110

Ser Ala Pro Phe Ser Phe Leu Ser Asn Val Lys Tyr Asn Phe Met Arg
            115                 120                 125

Ile Ile Lys Tyr Glu Phe Ile Leu Asn Asp Ala Leu Asn Gln Ser Ile
130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270
```

(2) INFORMATION FOR SEQ ID NO: 8:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..477

(xi) SEQUENCE DESCRIPTION: SEQ ID NO: 8:

```
TCA GCA CCT TTT AGC TTC CTG AGC AAT GTG AAA TAC AAC TTT ATG AGG          48
Ser Ala Pro Phe Ser Phe Leu Ser Asn Val Lys Tyr Asn Phe Met Arg
        275                 280                 285

ATC ATC AAA TAC GAA TTC ATC CTG AAT GAC GCC CTC AAT CAA AGT ATA          96
Ile Ile Lys Tyr Glu Phe Ile Leu Asn Asp Ala Leu Asn Gln Ser Ile
    290                 295                 300

ATT CGA GCC AAT GAT CAG TAC CTC ACG GCT GCT GCA TTA CAT AAT CTG         144
Ile Arg Ala Asn Asp Gln Tyr Leu Thr Ala Ala Ala Leu His Asn Leu
305                 310                 315                 320

GAT GAA GCA GTG AAA TTT GAC ATG GGT GCT TAT AAG TCA TCA AAG GAT         192
Asp Glu Ala Val Lys Phe Asp Met Gly Ala Tyr Lys Ser Ser Lys Asp
                325                 330                 335

GAT GCT AAA ATT ACC GTG ATT CTA AGA ATC TCA AAA ACT CAA TTG TAT         240
Asp Ala Lys Ile Thr Val Ile Leu Arg Ile Ser Lys Thr Gln Leu Tyr
            340                 345                 350

GTG ACT GCC CAA GAT GAA GAC CAA CCA GTG CTG CTG AAG GAG ATG CCT         288
Val Thr Ala Gln Asp Glu Asp Gln Pro Val Leu Leu Lys Glu Met Pro
        355                 360                 365

GAG ATA CCC AAA ACC ATC ACA GGT AGT GAG ACC AAC CTC CTC TTC TTC         336
Glu Ile Pro Lys Thr Ile Thr Gly Ser Glu Thr Asn Leu Leu Phe Phe
    370                 375                 380

TGG GAA ACT CAC GGC ACT AAG AAC TAT TTC ACA TCA GTT GCC CAT CCA         384
Trp Glu Thr His Gly Thr Lys Asn Tyr Phe Thr Ser Val Ala His Pro
385                 390                 395                 400

AAC TTG TTT ATT GCC ACA AAG CAA GAC TAC TGG GTG TGC TTG GCA GGG         432
Asn Leu Phe Ile Ala Thr Lys Gln Asp Tyr Trp Val Cys Leu Ala Gly
                405                 410                 415

GGG CCA CCC TCT ATC ACT GAC TTT CAG ATA CTG GAA AAC CAG GCG TAG         480
Gly Pro Pro Ser Ile Thr Asp Phe Gln Ile Leu Glu Asn Gln Ala
            420                 425                 430
```

(2) INFORMATION FOR SEQ ID NO: 9:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO: 9:

```
Ser Ala Pro Phe Ser Phe Leu Ser Asn Val Lys Tyr Asn Phe Met Arg
 1               5                  10                  15

Ile Ile Lys Tyr Glu Phe Ile Leu Asn Asp Ala Leu Asn Gln Ser Ile
            20                  25                  30

Ile Arg Ala Asn Asp Gln Tyr Leu Thr Ala Ala Ala Leu His Asn Leu
        35                  40                  45

Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125
```

```
Asn Leu Phe Ile Ala Thr Lys Gln Asp Tyr Trp Val Cys Leu Ala Gly
    130                 135                 140

Gly Pro Pro Ser Ile Thr Asp Phe Gln Ile Leu Glu Asn Gln Ala
145                 150                 155

(2) INFORMATION FOR SEQ ID NO: 10:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ix) FEATURE:
         (A) NAME/KEY: CDS
         (B) LOCATION: 1..807

(xi) SEQUENCE DESCRIPTION: SEQ ID NO: 10:

ATG GCA GAA GTA CCT GAG CTC GCC AGT GAA ATG ATG GCT TAT TAC AGT       48
Met Ala Glu Val Pro Glu Leu Ala Ser Glu Met Met Ala Tyr Tyr Ser
                    165                 170                 175

GGC AAT GAG GAT GAC TTG TTC TTT GAA GCT GAT GGC CCT AAA CAG ATG       96
Gly Asn Glu Asp Asp Leu Phe Phe Glu Ala Asp Gly Pro Lys Gln Met
                180                 185                 190

AAG TGC TCC TTC CAG GAC CTG GAC CTC TGC CCT CTG GAT GGC GGC ATC      144
Lys Cys Ser Phe Gln Asp Leu Asp Leu Cys Pro Leu Asp Gly Gly Ile
            195                 200                 205

CAG CTA CGA ATC TCC GAC CAC CAC TAC AGC AAG GGC TTC AGG CAG GCC      192
Gln Leu Arg Ile Ser Asp His His Tyr Ser Lys Gly Phe Arg Gln Ala
        210                 215                 220

GCG TCA GTT GTT GTG GCC ATG GAC AAG CTG AGG AAG ATG CTG GTT CCC      240
Ala Ser Val Val Val Ala Met Asp Lys Leu Arg Lys Met Leu Val Pro
225                 230                 235                 240

TGC CCA CAG ACC TTC CAG GAG AAT GAC CTG AGC ACC TTC TTT CCC TTC      288
Cys Pro Gln Thr Phe Gln Glu Asn Asp Leu Ser Thr Phe Phe Pro Phe
                245                 250                 255

ATC TTT GAA GAA GAA CCT ATC TTC TTT GAC ACA TGG GAT AAC GAG GCT      336
Ile Phe Glu Glu Glu Pro Ile Phe Phe Asp Thr Trp Asp Asn Glu Ala
            260                 265                 270

TAT GTG CAC GAT GCA CCT GTA CGA TCA CTG AAC TGC ACG CTC CGG GAC      384
Tyr Val His Asp Ala Pro Val Arg Ser Leu Asn Cys Thr Leu Arg Asp
        275                 280                 285

TCA CAG CAA AAA AGC TTG GTG ATG TCT GGT CCA TAT GAA CTG AAA GCT      432
Ser Gln Gln Lys Ser Leu Val Met Ser Gly Pro Tyr Glu Leu Lys Ala
    290                 295                 300

CTC CAC CTC CAG GGA CAG GAT ATG GAG CAA CAA GTG GTG TTC TCC ATG      480
Leu His Leu Gln Gly Gln Asp Met Glu Gln Gln Val Val Phe Ser Met
305                 310                 315                 320

TCC TTT GTA CAA GGA GAA GAA AGT AAT GAC AAA ATA CCT GTG GCC TTG      528
Ser Phe Val Gln Gly Glu Glu Ser Asn Asp Lys Ile Pro Val Ala Leu
                325                 330                 335

GGC CTC AAG GAA AAG AAT CTG TAC CTG TCC TGC GTG TTG AAA GAT GAT      576
Gly Leu Lys Glu Lys Asn Leu Tyr Leu Ser Cys Val Leu Lys Asp Asp
            340                 345                 350

AAG CCC ACT CTA CAG CTG GAG AGT GTA GAT CCC AAA AAT TAC CCA AAG      624
Lys Pro Thr Leu Gln Leu Glu Ser Val Asp Pro Lys Asn Tyr Pro Lys
        355                 360                 365

AAG AAG ATG GAA AAG CGA TTT GTC TTC AAC AAG ATA GAA ATC AAT AAC      672
Lys Lys Met Glu Lys Arg Phe Val Phe Asn Lys Ile Glu Ile Asn Asn
    370                 375                 380
```

```
AAG CTG GAA TTT GAG TCT GCC CAG TTC CCC AAC TGG TAC ATC AGC ACC   720
Lys Leu Glu Phe Glu Ser Ala Gln Phe Pro Asn Trp Tyr Ile Ser Thr
385                 390                 395                 400

TCT CAA GCA GAA AAC ATG CCC GTC TTC CTG GGA GGG ACC AAA GGC GGC   768
Ser Gln Ala Glu Asn Met Pro Val Phe Leu Gly Gly Thr Lys Gly Gly
                405                 410                 415

CAG GAT ATA ACT GAC TTC ACC ATG CAA TTT GTG TCT TCC TAA           810
Gln Asp Ile Thr Asp Phe Thr Met Gln Phe Val Ser Ser
                420                 425
```

(2) INFORMATION FOR SEQ ID NO: 11:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO: 11:

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265
```

(2) INFORMATION FOR SEQ ID NO: 12:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..459

(xi) SEQUENCE DESCRIPTION: SEQ ID NO: 12:

```
GCA CCT GTA CGA TCA CTG AAC TGC ACG CTC CGG GAC TCA CAG CAA AAA      48
Ala Pro Val Arg Ser Leu Asn Cys Thr Leu Arg Asp Ser Gln Gln Lys
                275                 280                 285

AGC TTG GTG ATG TCT GGT CCA TAT GAA CTG AAA GCT CTC CAC CTC CAG      96
Ser Leu Val Met Ser Gly Pro Tyr Glu Leu Lys Ala Leu His Leu Gln
            290                 295                 300

GGA CAG GAT ATG GAG CAA CAA GTG GTG TTC TCC ATG TCC TTT GTA CAA     144
Gly Gln Asp Met Glu Gln Gln Val Val Phe Ser Met Ser Phe Val Gln
        305                 310                 315

GGA GAA GAA AGT AAT GAC AAA ATA CCT GTG GCC TTG GGC CTC AAG GAA     192
Gly Glu Glu Ser Asn Asp Lys Ile Pro Val Ala Leu Gly Leu Lys Glu
    320                 325                 330

AAG AAT CTG TAC CTG TCC TGC GTG TTG AAA GAT GAT AAG CCC ACT CTA     240
Lys Asn Leu Tyr Leu Ser Cys Val Leu Lys Asp Asp Lys Pro Thr Leu
335                 340                 345                 350

CAG CTG GAG AGT GTA GAT CCC AAA AAT TAC CCA AAG AAG AAG ATG GAA     288
Gln Leu Glu Ser Val Asp Pro Lys Asn Tyr Pro Lys Lys Lys Met Glu
                355                 360                 365

AAG CGA TTT GTC TTC AAC AAG ATA GAA ATC AAT AAC AAG CTG GAA TTT     336
Lys Arg Phe Val Phe Asn Lys Ile Glu Ile Asn Asn Lys Leu Glu Phe
            370                 375                 380

GAG TCT GCC CAG TTC CCC AAC TGG TAC ATC AGC ACC TCT CAA GCA GAA     384
Glu Ser Ala Gln Phe Pro Asn Trp Tyr Ile Ser Thr Ser Gln Ala Glu
        385                 390                 395

AAC ATG CCC GTC TTC CTG GGA GGG ACC AAA GGC GGC CAG GAT ATA ACT     432
Asn Met Pro Val Phe Leu Gly Gly Thr Lys Gly Gly Gln Asp Ile Thr
    400                 405                 410

GAC TTC ACC ATG CAA TTT GTG TCT TCC TAA                             462
Asp Phe Thr Met Gln Phe Val Ser Ser
415                 420
```

(2) INFORMATION FOR SEQ ID NO: 13:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO: 13:

```
Ala Pro Val Arg Ser Leu Asn Cys Thr Leu Arg Asp Ser Gln Gln Lys
 1               5                  10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60
```

```
                                      -continued

Lys Asn Leu Tyr Leu Ser Cys Val Leu Lys Asp Asp Lys Pro Thr Leu
 65              70                  75                  80

Gln Leu Glu Ser Val Asp Pro Lys Asn Tyr Pro Lys Lys Lys Met Glu
             85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150
```